(12) United States Patent
Sotoyama et al.

(10) Patent No.: US 7,176,014 B2
(45) Date of Patent: Feb. 13, 2007

(54) SOLID CULTURE MEDIUM AND METHOD FOR PREPARING THE SAME

(75) Inventors: Kazuyoshi Sotoyama, Zama (JP); Yasuo Fukuwatari, Zama (JP); Yoichiro Yano, Zama (JP); Kenji Kiyotaki, Zama (JP); Minoru Nakagawa, Zama (JP); Kenichiro Karino, Zama (JP); Kazue Sasaki, Zama (JP)

(73) Assignee: Morinaga Milk Industry Co., Ltd., Tokyo (JP)

( * ) Notice: Subject to any disclaimer, the term of this patent is extended or adjusted under 35 U.S.C. 154(b) by 690 days.

(21) Appl. No.: 10/432,089

(22) PCT Filed: Aug. 9, 2001

(86) PCT No.: PCT/JP01/06872

§ 371 (c)(1),
(2), (4) Date: May 20, 2003

(87) PCT Pub. No.: WO02/061051

PCT Pub. Date: Aug. 8, 2002

(65) Prior Publication Data

US 2004/0041123 A1    Mar. 4, 2004

(30) Foreign Application Priority Data

Jan. 29, 2001  (JP) .............................. 2001-020606

(51) Int. Cl.
*C12N 1/12* (2006.01)
(52) U.S. Cl. ................ 435/253.6; 435/256.8; 435/404; 435/252.1
(58) Field of Classification Search ............. 435/252.1, 435/256.8, 404, 253.6
See application file for complete search history.

(56) References Cited

U.S. PATENT DOCUMENTS 3,935,067 A    1/1976  Thayer
3,941,658 A *  3/1976  Lameris et al. ............... 435/32
4,945,053 A *  7/1990  Ito et al. ..................... 435/209
6,258,586 B1*  7/2001  Jussila et al. ............... 435/252
6,399,056 B1*  6/2002  Ono et al. ............. 424/93.462

FOREIGN PATENT DOCUMENTS

| JP | 54-8786 | 1/1979 |
| JP | 60-19988 | 5/1985 |
| JP | 60161410 | 8/1985 |
| JP | 62-087091 | 4/1987 |
| JP | 5-260952 | 10/1993 |
| JP | 6-311880 | 11/1994 |
| JP | 06-311880 | 11/1994 |
| JP | 8-182494 | 7/1996 |
| JP | 08182494 | 7/1996 |
| JP | 10-248555 | 9/1998 |

OTHER PUBLICATIONS

Office Action from Japanese Patent Office, mailed May 17, 2005 for corresponding Japanese Patent Application No. 2002-561608.

* cited by examiner

*Primary Examiner*—Leon B. Lankford, Jr.
(74) *Attorney, Agent, or Firm*—Knobbe, Martens, Olson & Bear, LLP

(57) ABSTRACT

A solid medium having a 10 minute-average water absorption rate of at least 0.05 ml/minute, which is obtainable by a method for producing a solid medium comprising the steps of dissolving components of the solid medium other than solvent water into the solvent water, solidifying the obtained solution, and drying the solidified medium to remove water, wherein water is removed in such an amount that the solid medium after the removal of water should have the 10 minute-average water absorption rate of at least 0.05 ml/minute, and the amount of the solvent water is larger than a prescribed amount by an amount almost equal to the amount of the water to be removed. The solid medium does not cause growth inhibition of microorganisms due to drying, shows a superior water absorption rate to enable application of a larger amount of a sample in a short period of time, and is suitable for quick and accurate measurement tests of microbial numbers.

6 Claims, No Drawings

SOLID CULTURE MEDIUM AND METHOD FOR PREPARING THE SAME

RELATED APPLICATIONS

This application is the U.S. National Phase under 35U.S.C. §371 of International Application PCT/JP 01/06872, filed Aug. 9, 2001, which was published in a language other than English, which claims priority of Japanese Patent Application No. 2001-20606, filed Jan. 29, 2001 all of which are incorporated herein by reference in their entirety.

TECHNICAL FIELD

The present invention relates to a solid medium used for growth and tests of various microorganisms and so forth and a method for producing the same.

BACKGROUND ART

As an example of dried solid media, a dried solid medium is conventionally known which is prepared by lyophilizing a medium poured into a plastic dish and solidified (JP 60-19988B, referred to as "Prior art 1" hereinafter).

Further, there is also a known dried solid medium in the form of a film, which contains a gelling agent such as agar and is easily substantially restored to a previous state before it is formed into film by adding sterilized water (JP 6-311880A, referred to as "Prior art 2" hereinafter).

However, these conventional materials have the following problems.

Prior art 1 and Prior art 2 mentioned above are used in order to improve storage stability of media and the media are dried so that a water content in the compositions of finally obtained solid medium becomes 50% or less. Therefore, they have a problem that they require a long period of time as long as about 3 hours for full restoration of the media upon use.

Further, since the dried solid media obtained according to the aforementioned conventional techniques require a long period of time for restoration as described above, restoration in a relatively short period such as 1 to 10 minutes results in insufficient restoration. If such media are used for microorganism tests, growth of *Staphylococcus aureus* ATCC 6538P, *Bacillus stearothermophilus* var. *calidolactis* NIZO C953 etc., which are important bacterial species in microorganism tests of foodstuffs and so forth, is partially inhibited due to the insufficient restoration of the medium, resulting in inaccurate measurement of the number of microorganisms, as demonstrated by the Test Examples mentioned later.

That is, the conventional dried solid media have a problem that they require a long period of time for restoration, and thus they are not suitable for quick and accurate measurement tests of microbial numbers.

Further, it is known that a solid medium is dried in order to remove excessive moisture on its surface after its production. Since this drying process removes a part of solvent water from the solid medium prepared in a prescribed composition, water content of the medium upon actual culture of microorganisms should significantly differ from the prescribed content in the composition identifying the solid medium. Influences of medium-drying on the culture of microorganisms cannot be ignored. For example, it is known that growth of microorganisms is sometimes degraded due to drying etc., even when a medium is stored in a test tube with a cotton plug for several weeks. Moreover, uncontrolled removal of water sometimes makes the composition of solid media inconstant. Therefore, reproducible and accurate results may not be obtained in culture tests of microorganisms, especially those of microorganisms that are likely to be affected by the water content of medium.

DISCLOSURE OF THE INVENTION

An object of the present invention is to provide a solid medium which shows a superior water absorption rate to enable application of a large amount of sample in a short period of time and is suitable for quick and accurate measurement tests of microbial numbers and to provide a method for producing the same.

The inventors of the present invention assiduously studied in view of the aforementioned problems of the prior art. As a result, they obtained a solid medium by dissolving components of the solid medium into the solvent water whose amount is larger than a prescribed amount, solidifying the obtained solution and drying the solidified medium to remove water in an amount almost equal to the excessive amount of the solvent water. They have found that the medium does not cause growth inhibition of microorganisms due to drying. They have also found that it shows superior water absorption rate to enable application of a large amount of a sample in a short period of time and is suitable for quick and accurate measurement tests of microbial numbers. Thus, they accomplished the present invention.

The present invention provides a solid medium having a 10 minute-average water absorption rate of at least 0.05 ml/minute (also referred to as the "solid medium of the present invention" hereinafter), which is obtainable by a method for producing a solid medium comprising the steps of dissolving components of the solid medium other than solvent water into the solvent water, solidifying the obtained solution, and drying the solidified medium to remove water, wherein water is removed in such an amount that the solid medium after the removal of water should have the 10 minute-average water absorption rate of at least 0.05 ml/minute, and the amount of the solvent water is larger than a prescribed amount by an amount almost equal to the amount of the water to be removed.

In the solid medium of the present invention, the amount of the water to be removed is preferably at least 5% of the solvent water, more preferably at least 30% of the solvent water.

The solid medium of the present invention preferably has a water content of at least 90%.

The present invention also provides a method for producing a solid medium comprising the steps of dissolving components of the solid medium other than solvent water into the solvent water, solidifying the obtained solution and drying the solidified medium to remove water, wherein water is removed in such an amount that the solid medium after the removal of water should have a 10 minute-average water absorption rate of at least 0.05 ml/minute, and the amount of the solvent water is larger than a prescribed amount by an amount almost equal to the amount of the water to be removed.

In the production method of the present invention, the amount of the water to be removed is preferably at least 5% of the solvent water, more preferably at least 30% of the solvent water.

In the present specification, a solid medium means a medium that is in a solid state at the time of use, for example, a plate medium, slant medium and so forth, which are solidified with a gelling agent such as agar.

A medium is generally identified (defined) by its composition. Thus, the prescribed amount of solvent water is an amount of water in such a composition used for the identification of the medium. The prescribed amount of solvent water means an amount of water added in order to dissolve each component of the solid medium other than solvent water, and when a component of the solid medium is specified as an aqueous solution, the amount of water in this component is not included.

The 10 minute-average water absorption rate is calculated in accordance with the following equation by using A and B measured as follows. Total weight (B) of a sample plate (circular shape, outer diameter: 9 cm, inner diameter: 8.6 cm (area: 58.1 cm$^2$), amount of medium: 15 g) is measured, and water absorption is started by adding 10 ml of ion-exchanged water onto the plate medium. After 10 minutes, water that has not been absorbed is discarded, moisture on a dish wall is wiped off, and the total weight (A) of the sample plate after the water absorption is measured. The measurement is performed at 25° C. When the area of the sample plate differs from the aforementioned area, the test is performed by using ion exchanged water in an amount of 10 ml per above-defined area, and the result is converted into a water absorption rate per above-mentioned area.

Water absorption rate (ml/minute)=$(A-B)/10$

The amount of water removed by drying is calculated by measuring the weight loss due to drying. That is, the weight loss due to drying, i.e., so-called water loss (c), can be obtained from the medium weight before the drying (a) and the medium weight after the drying (b) in accordance with an equation of a−b=c. Then, a ratio of the removed water, i.e., percentage of water removed by drying (e, %) can be obtained from the total amount of added solvent water (d) and the aforementioned weight loss due to drying (c) in accordance with the following equation.

$e(\%)=c/d\times100$

A water content of solid medium means a percentage of water content (%) defined as (amount of water in solid medium)/(amount of solid content+amount of water)×100. Here, both the amount of water and the solid content are represented in weight.

BEST MODE FOR CARRYING OUT THE INVENTION

A medium is a nutriment for growing or proliferating microorganisms such as bacteria, yeasts and molds, and it is also their growing environment. A medium usually contains, as medium components, a saccharide such as glucose and lactose, a nitrogen source such as amino acids, peptone, nitrates and ammonium salts, inorganic salts such as those of potassium, phosphorus and magnesium, a growth factor such as vitamins and so forth. Media are roughly classified into liquid media in which medium components are simply dissolved in solvent water and solid media solidified by addition of a gelling agent into liquid media. The present invention provides a solid medium, which is, as defined above, a medium (culture medium) in a solid state at the time of use, for example, a plate medium, slant medium or the like, produced by solidifying with a gelling agent such as agar.

Examples of the gelling agent include agar, gelatin, gellan gum, carrageenan and so forth.

Specific examples of the composition of the solid medium of the present invention include the compositions of the followings: the nutrient agar medium, the standard agar medium, the deoxycholate agar medium, the E.M.B. medium, the Endo medium, the plate count agar medium with B.C.P., the mannitol salt agar with egg yolk, the potato dextrose agar medium, the Violet red bile lactose (VRBL) agar medium, the yeast extract-glucose-chloramphenicol agar medium, the Acidified MRS medium, Medium M17, the Baird-Parker agar medium (ETGP agar medium) and so forth, which are defined in microorganism test methods described in the Japanese Food Sanitation Law, the Japan Pharmacopoeia, the International Diary Federation Standard (IDF STANDARD) and so forth ["Nyuseihin Shikenhou Chukai (Commentary of Test Methods of Dairy Products)", Ed. by the Pharmaceutical Society of Japan, pp.111–125, Apr. 10, 1990, Kanehara Shuppan Co., Ltd. (Reference 1); "IDF STANDARD (Revised Version of 1991)", p.306, p.470, pp.645–647, Dec. 25, 1991, published by International Dairy Federation of Japan (Reference 2); "Shin Saikin Baichi-gaku Koza Ge II (Lecture of Culture Medium Science for Bacteria, Vol. 2, II)", Second edition, Editorship: Sakazaki Toshikazu, pp.62–63, Aug. 15, 1996, Kindai Shuppan Co., Ltd. (Reference 3)).

For reference, the prescribed amounts of respective components contained in the aforementioned solid media described in Reference 1 are mentioned below.

Prescribed amounts of components in the solid medium composition of the nutrient agar medium (pH 7.0 to 7.4) are 5 g of meat extract, 10 g of peptone, 1 to 2 g of sodium chloride (NaCl), 12 to 15 g of agar and 1000 ml (1 liter) of purified water (solvent water ).

Prescribed amounts of components in the solid medium composition of the standard agar medium (pH 6.8 to 7.2) are 2.5 g of yeast extract, 5 g of peptone, 1 g of glucose, 15 g of agar and 1000 ml (1 liter) of purified water (solvent water).

Prescribed amounts of each component in the solid medium composition of the deoxycholate agar medium (pH 7.0 to 7.4) are 10 g of peptone, 10 g of lactose, 1 g of sodium deoxycholate, 5 g of sodium chloride (NaCl), 2 g of $K_2HPO_4$, 0.033 g of Neutral Red, 2 g of ferric ammonium citrate, 15 g of agar and 1000 ml (1 liter) of purified water (solvent water).

Prescribed amounts of components in the solid medium composition of the E.M.B. medium (pH 6.6 to 7.0) are 10 g of peptone, 10 g of lactose, 2 g of $K_2HPO_4$, 0.4 g of Eosin Y, 0.065 g of Methylene Blue, 18 g of agar and 1000 ml (1 liter) of purified water (solvent water).

Prescribed amounts of components in the solid medium composition of the Endo medium (pH 7.0 to 7.4) are 10 g of peptone, 3 g of meat extract, 10 g of lactose, 1.6 g of $Na_2SO_3$, 0.1 g of Basic Fuchsine, 15 g of agar and 1000 ml (1 liter) of purified water (solvent water).

Prescribed amounts of components in the solid medium composition of the plate count agar medium with B.C.P. (pH 6.0 to 7.0) are 2.5 g of yeast extract, 5 g of peptone, 1 g of glucose, 1 g of Tween 80, 0.1 g of L-cysteine, 0.06 g of Bromocresol Purple, 15 g of agar and 1000 ml (1 liter) of purified water (solvent water).

Prescribed amounts of components in the solid medium composition of the mannitol salt agar with egg yolk [pH 7.2 to 7.6, where 50 to 60ml of fresh egg yolk solution (obtained by dissolving egg yolk into the same amount of physiological saline) is added after sterilization with high pressure steam and before pouring the medium into plate] are 2.5 g of meat extract, 10 g of peptone, 10 g of mannitol, 75 g of sodium chloride (NaCl), 0.025 g of Phenol Red, 15 g of agar and 1000 ml (1 liter) of purified water (solvent water).

Prescribed amounts of components in the solid medium composition of the potato dextrose agar (pH 5.6 to 5.7) are 200 g of potato infusion, 20 g of glucose, 15 g of agar and 1000 ml (1 liter) of purified water (solvent water).

Prescribed amounts of respective components contained in the solid media described in Reference 2 are mentioned hereafter.

Prescribed amounts of components in the solid medium composition of the Violet red bile salt lactose (VRBL) agar medium (pH 7.4±0.1) are 7 g of peptone, 3 g of yeast extract, 10 g of lactose ($C_{12}H_{22}O_{11}.H_2O$), 5 g of sodium chloride (NaCl), 1.5 g of bile acid salt, 0.03 g of Neutral Red, 0.002 g of Crystal Violet, 12 to 18 g of agar and 1000 ml (1 liter) of water (solvent water).

Prescribed amounts of components in the solid medium composition of the yeast extract-glucose-chloramphenicol agar medium (pH 6.6) are 5 g of yeast extract, 20 g of glucose ($C_6H_{12}O_6$), 0.1 g of chloramphenicol ($C_{11}H_{12}Cl_2N_2O_5$) or oxytetracycline ($C_{22}H_{30}N_2O_{11}$), 12 to 15 g of agar and 1000 ml (1 liter) of water (solvent water).

Prescribed amounts of components in the solid medium composition of the acidified MRS medium (adjusted to pH 5.4 with acetic acid) are 10 g of Peptone 1 (trypsin-digested product of casein), 10 g of meat extract, 5 g of yeast extract (powder), 20 g of glucose ($C_6H_{12}O_6$), 1 ml of Tween 80 (sorbitan mono-oleate), 2 g of dipotassium hydrogenorthophosphate ($K_2HPO_4$), 5 g of sodium acetate trihydrate ($CH_3CO_2Na.3H_2O$), 2 g of diammonium citrate ($C_6H_6O_7(NH_4)_2$), 0.2 g magnesium sulfate heptahydrate ($MgSO_4.7H_2O$), 0.05 g of manganese sulfate tetrahydrate ($MnSO_4.4H_2O$), 9 to 18 g of agar and 1000 ml (1 liter) of water (solvent water).

Prescribed amounts of components in the solid medium composition of Medium M17 [pH 7.1 to 7.2, where lactose ($C_{12}H_{22}O_{11}$) is added as a sterilized 10% lactose ($C_{12}H_{22}O_{11}$) aqueous solution after sterilization with high pressure steam and before pouring the medium into plate] are 2.50 g of Peptone 1 (trypsin-digested product of casein), 2.50 g of Peptone 2 (pepsin-digested product of meat), 5.00 g of Peptone 3 (papain-digested product of soybean), 2.50 g of yeast extract (powder), 5.00 g of meat extract, 19.00 g of β-glycerophosphoric acid salt (disodium salt, $C_6H_7O_6PNa_2$), 0.25 g of magnesium sulfate heptahydrate ($MgSO_4.7H_2O$), 0.50 g of ascorbic acid ($C_6H_8O_6$), 5 g of lactose ($C_{12}H_{22}O_{11}$), 9 to 18 g of agar and 1000 ml (1 liter) of water (solvent water).

Prescribed amounts of components contained in the solid medium described in Reference 3 are mentioned hereafter.

Prescribed amounts of components in the solid medium composition of the Baird-Parker agar medium (ETGP agar medium, pH 6.8, where10 ml of1% potassium tellurite aqueous solution and 50 ml of 50% egg yolk emulsion are added after sterilization with high pressure steam and before pouring the medium into plate) are 10 g of peptone, 5 g of meat extract, 1 g of yeast extract, 5 g of lithium chloride, 12 g of glycine, 10 g of sodium pyruvate, 17 g of agar and 1000 ml (1 liter) of purified water (solvent water).

The method for producing a solid medium of the present invention is explained hereafter.

In the method for producing a solid medium of the present invention, dissolution of components of the solid medium into solvent water and solidification of the solution can be performed in the same manner as in the production of usual solid media except that the amount of the solvent water is larger than its prescribed amount and that water is removed by drying after the solidification. For example, prescribed amounts of medium components described in literature etc. or newly identified as a solid medium composition (defined) can be dissolved in solvent water; after adjusting pH when required, a gelling agent can be added to the solution; and the mixture can be heated to dissolve the gelling agent, sterilized, poured into a vessel like a dish and solidified.

The amount of water to be removed is such an amount that the 10 minute-average water absorption rate of the solid medium should become at least 0.05 ml/minute after the removal of water. Although this amount may vary depending on the medium composition (especially depending on the gelling agent), it can be determined by producing media containing solvent water in various excessive amounts and measuring their 10 minute-average water absorption rates in such a manner as described in Test Example 3 mentioned later.

The amount of water to be removed is preferably at least 5% of the solvent water, more preferably at least 30% of the solvent water.

When water is removed in above-mentioned manner from a solid medium prepared by using a prescribed amount of solvent water, the amount of water contained in the solid medium may be significantly reduced after the removal of water, resulting in growth inhibition of microorganisms due to drying. According to the present invention, the amount of solvent water in the solid medium is determined beforehand to be larger than the prescribed one, so that water is contained in the solid medium in an amount corresponding to the prescribed amount after the removal of water. Therefore, the amount of solvent water is larger than the prescribed amount by an amount almost equal to that of water to be removed. The amount almost equal to that of water to be removed herein means the amount at which, the amount obtained by subtracting the amount of water to be removed from the amount of the total added solvent water including the prescribed amount and the additional amount of water, should become substantially equal to (usually, 97 to 103%) the prescribed amount of water.

Usually, the additional amount of the solvent water is 5 to 150% when the amount of solvent water (prescribed amount of solvent water) in a composition described literature etc., or in a composition newly identified as a solid medium composition, is taken as 100%. This amount of solvent water is formulated in addition to the prescribed amount of water. This enables the production of the solid medium of the present invention which contains a prescribed amount of water and has a sufficient water absorption rate, as an end product obtained by removing solvent water by drying.

When an agar is used as the gelling agent, the concentration of the added agar is preferably 1.0 to 3% (by weight) when the aforementioned prescribed amount of solvent water is taken as 100%. Further, the heating for dissolution is preferably performed at a temperature of 100° C. or higher, since agar is fully dissolved at such a temperature. If the heating is performed at 121° C. for 15 minutes or more, sterilization can also be attained simultaneously with the dissolution. Sterilization may be performed in a conventional manner by using high pressure steam sterilization method or the like.

When dishes are used as the vessels, the solid medium is preferably poured into each dish in such an amount that the amount of the solid medium in each dish after the removal of water by drying should become 10 to 30 ml.

Examples of the drying method to remove water from the medium include reduced pressure drying method, vacuum evaporation method, warm air drying method, infrared drying method, high frequency drying method and so forth. However, the method is not limited to these.

The solid medium of the present invention has 10 minute-average water absorption rate of at least 0.05 ml/minute according to the definition mentioned above. If the solid medium shows water absorption of at least 0.5 ml for 10 minutes per one plate of the standard size defined above, it becomes possible to apply a large amount of a sample onto the solid medium in a short period of time. A solid medium showing the 10 minute-average water absorption rate of at least 0.05 ml/minute can be prepared by drying the medium to remove such an appropriate amount of water as described above. The amount of medium per exposed area (area in contact with air) of the solid medium can be such an amount that the 10 minute-average water absorption rate in the aforementioned range can be obtained. If the amount of the medium is too small, a sufficient 10 minute-average water absorption rate may not be obtained.

Since the solid medium of the present invention contains solvent water in an amount almost equal to the prescribed amount after the removal of water, growth inhibition of microorganisms resulting from drying is not observed on it. This is because a prescribed amount of solvent water in a composition identifying a solid medium is determined so that a microorganism to be cultured can grow. Alternatively, it is because a medium having a composition that does not cause growth inhibition of a microorganism to be cultured is selected.

The solid medium preferably has a water content of at least 90%. Such water content enables culture of microorganism requiring high water content. For example, since growth of a microorganism such as *Staphylococcus aureus* ATCC 6538P is almost completely inhibited in water content lower than 90% as demonstrated in the Test Examples mentioned later, it is necessary to keep water content of at least 90% in the solid medium in order to culture the microorganism.

Furthermore, the solid medium of the present invention is suitable for culturing microorganisms that are relatively weak to dryness, but important for microorganism tests of foodstuffs and so forth, such as *Staphylococcus aureus* ATCC 6538P and *Bacillus stearothermophilus* var. *calidolactis* NIZO C953, without causing any growth inhibition thereof. As described above, the solid medium of the present invention is dried in a state that it contains solvent water in an amount larger than the prescribed amount. Therefore, it maintains a sufficient water absorption rate and does not cause growth inhibition due to drying.

In order to make it much easier to understand the method for producing a solid medium of the present invention, it is explained by exemplifying a method for producing the standard agar medium described in Reference 1 mentioned above.

Namely, prescribed amounts of components in the solid medium composition of the standard agar medium are 2.5 g of yeast extract, 5 g of peptone, 1 g of glucose, 15 g of agar and 1000 ml of purified water (solvent water), as described in Reference 1.

Therefore, the component of 2.5 g of yeast extract, 5 g of peptone and 1 g of glucose are dissolved in solvent water whose amount is preferably 5 to 150% (50 to 1500 ml) larger than the prescribed amount (1000 ml) to obtain a dissolved solution in an amount from about 1050 ml to 2500 ml. The dissolved solution is adjusted to pH 6.8 to 7.2. 15 g of agar is added to the solution and the mixture is heated at 121° C. for 15 minutes by the high pressure steam sterilization method to dissolve and sterilize simultaneously.

The sterilized medium is aseptically poured into dishes in an amount of 16 to 38 g per dish, and solidified by cooling. The solidified medium is then dried by the reduced pressure drying method under a pressure of $10^3$ Pa using a dryer (LABCONCO) to remove solvent water.

By the aforementioned method to remove water by drying, the additional amount of water is removed to produce a solid medium which has the 10 minute-average water absorption rate of at least 0.05 ml/minute.

The solid medium produced by the aforementioned method does not cause growth inhibition of microorganisms resulting from drying. Moreover, it shows a superior water absorption rate and enables application of a large amount of a sample in a short period of time and is suitable for quick and accurate measurement tests of microbial numbers.

EXAMPLES

The present invention is explained in more detail by the following examples. However, the present invention is not limited to the following examples.

Example 1

2.5 g of yeast extract (Oriental Yeast), 5 g of peptone (Difco) and 1 g of glucose (Wako Pure Chemical Industries) were dissolved in 1200 ml of solvent water which contains 20% (200 ml) excess water in addition to the prescribed amount of solvent water (purified water, 1000 ml), which was taken as 100%, in a known solid medium composition to obtain about 1200 ml of a dissolved solution. The solution was adjusted to pH 7.2 by using 0.1 mol/l sodium hydroxide solution. 15 g of agar (Ina Shokuhin Kogyo) was added to the solution and the mixtures was heated at 121° C. for 15 minutes by using an autoclave (Iwatate Iryo Kikai Seisakusho) to attain dissolution and sterilization at the same time.

The sterilized solid medium was poured into each plastic dish having a diameter of 9 cm (Eiken Kizai) in an amount of 18 g per dish in a sterile room, solidified by cooling and dried at a pressure of $10^3$ Pa according to the reduced pressure drying method using a drier (LABCONCO) to remove 3 ml of water. As a result, solid medium plates each containing 15 g of the medium were obtained.

The aforementioned removal of water corresponded to removal of the total amount of the solvent water (200 ml) formulated in addition to the prescribed amount of water, i.e., removal of about 17% (200 ml) of the total amount (1200 ml) of the added solvent water (purified water), which was taken as 100%, by drying.

Thus, the water content of the solid medium has been adjusted to about 98% by the aforementioned removal of water.

The solid medium (the nutrient agar medium) plates produced as described above were tested by the method described later, and they were found to have the 10 minute-average water absorption rate of 0.15 ml/minute. It has been found that the medium is a solid medium capable of application of a large amount of a sample in a short period of time and which does not show growth inhibition caused by drying, whereby it is suitable for quick and accurate measurement tests of microbial numbers.

Example 2

2.5 g of meat extract (Merck),10 g of peptone (Difco), 75 g of sodium chloride (Wako Pure Chemical Industries), 10 g of mannitol (Wako Pure Chemical Industries) and 0.025 g of Phenol Red (Wako Pure Chemical Industries) were dissolved in 1066 ml of solvent water which contains 6.6% (66 ml) excess water in addition to the prescribed amount of solvent water (purified water, 1000 ml) taken as 100%, in a known solid medium composition, to obtain about 1066 ml of a dissolved solution. The dissolved solution was adjusted to pH 7.4 by using 0.1 mol/l sodium hydroxide solution. 15 g of agar (Ina Shokuhin Kogyo) was added to the solution and the mixture was heated at 121° C. for 15 minutes by using an autoclave (Iwatate Iryo Kikai Seisakusho) to attain dissolution and sterilization at the same time.

The sterilized solid medium was poured into each plastic dish having a diameter of 9 cm (Eiken Kizai) in an amount of 16 g per dish in a sterile room, solidified by cooling and dried at a pressure of $10^3$ Pa according to the reduced pressure drying method using a drier (LABCONCO) to remove about 1 ml of solvent water. As a result, solid medium plates each containing 15 g of the medium were obtained.

The aforementioned removal of water corresponded to removal of the total amount of the solvent water (66 ml) formulated in addition to the prescribed amount of water, i.e., removal of about 6% (66 ml) of the total amount (1066 ml) of the added solvent water (purified water) taken as 100%, was removed by drying.

Therefore, the water content of the solid medium has been adjusted to about 90% by the aforementioned removal of water.

The solid medium (the mannitol salt agar with egg yolk) plates produced as described above were tested by the method described later, and they were found to have the 10 minute-average water absorption rate of 0.07 ml/minute. It has been found that the medium is a solid medium which enables application of a large amount of a sample in a short period of time and which does not show microbial growth inhibition of *Staphyiococcus* bacteria caused by drying, whereby it is suitable for quick and accurate measurement tests of microbial numbers.

Example 3

A solid medium having a novel composition was prepared by modifying a composition of a known solid medium. 10 g of peptone (Difco), 5 g of meat extract (Merck) and 2 g of sodium chloride (Wako Pure Chemical Industries) were dissolved in 1200 ml of solvent water, which contains 33.3% (300 ml) of excess water in addition to a prescribed amount of 900 ml, taken as 100%, which was modified to a less amount than the prescribed amount of solvent water (purified water, 1000 ml) in a known solid medium composition, to obtain about 1200 ml of a dissolved solution. The dissolved solution was adjusted to pH 7.0 by using 0.1 mol/l sodium hydroxide solution. 15 g of agar (Ina Shokuhin Kogyo) was added to the solution and the mixture was heated at 121° C. for 15 minutes by using an autoclave (Iwatate Iryo Kikai Seisakusho) to attain dissolution and sterilization at the same time.

The sterilized solid medium was poured into each plastic dish having a diameter of 9 cm (Eiken Kizai) in an amount of 20 g per dish in a sterile room, solidified by cooling and dried at a pressure of $10^3$ Pa according to the reduced pressure drying method using a drier (LABCONCO) to remove 5 ml of solvent water. As a result, solid medium plates each containing 15 g of the medium were obtained.

The aforementioned removal water corresponded to removal of the total amount (300 ml) of the water formulated in addition to the prescribed amount of water, i.e., removal of about 25% (300 ml) of total amount (1200 ml) of the added solvent water(purified water), taken as 100%, by drying.

Thus, the water content of the solid medium has been adjusted to about 96% by the aforementioned removal of water.

The solid medium (nutrient agar medium) plates produced as described above were tested by the method described later, and they were found to have the 10 minute-average water absorption rate of 0.17 ml/minute. It has been found that the medium is a solid medium which enables application of a large amount of sample in a short period of time and which does not show microbial growth inhibition caused by drying, whereby it is suitable for quick and accurate measurement tests of microbial numbers.

Test Example 1

This test was performed to compare the present invention with the prior art by using results of microbial growth test as indexes.

(1) Preparation of Samples

Each of the following three kinds of samples was prepared in quintuplicate.

Sample 1: Solid medium produced in the same manner as in Example 1 of the present invention.

Sample 2: Solid medium produced in the same manner as in Example 1 of Prior Art 1 except that the type of the medium was changed to the nutrient agar medium, 15 ml of the medium was poured into each dish, 15 ml of water for restoration (sterilized water) was used, the solid medium was restored for 5 minutes and excessive water for restoration (free water) was discarded by decantation.

Sample 3: Solid medium produced in the same manner as in Example 1 of Prior Art 2 except that the type of the medium was changed to the nutrient agar medium, 15 ml of the medium was poured into each dish, 15 ml of water for restoration (sterilized water) was used, the solid medium was restored for 5 minutes and excessive water for restoration (free water) was discarded by decantation.

(2) Test Method

Microbial growth on each sample was examined by the following test method.

As test strains, *Staphylococcus aureus* ATCC 6538P obtained from the American Type Culture Collection, which is a depository of microorganisms, and *Bacillus stearothermophilus* var. *calidolactis* NIZO C953 obtained from the Netherlands Institute for Dairy Research (Nederlands Instituut voor Zuivelonderzoek, NIZO) were used.

Such a dilution of each test strain was prepared that, when 0.1 ml of the dilution was applied onto one standard agar medium plate prepared by using solvent water in the prescribed amount defined in the known solid medium composition, i.e., using solvent water in the prescribed amount defined in the known solid medium composition as it was, without any drying process and incubated at 37° C. for 48 hours, 100 colonies of the test strain should be obtained.

The solid medium composition of the standard agar medium is composed of 2.5 g of yeast extract, 5 g of peptone, 1 g of glucose, 15 g of agar and 1000 ml (prescribed amount of solvent water) of purified water.

The dilution of test strain in an amount of 0.1 ml was applied onto one plate of each sample and incubated at 37° C. for 48 hours, and number of appeared colonies was determined by visual inspection. The test was performed in quintuplicate, and an average of the numbers of colonies was calculated.

(3) Test Results

The results of this test are as shown in Table 1. As clearly seen from the results shown in Table 1, it was found that Sample 1 according to the present invention is superior to Samples 2 and 3 according to prior art, since *Staphylococcus aureus* ATCC 6538P and *Bacillus stearothermophilus* var. *calidolactis* NIZO C953, which are important bacteria for microorganism tests of foodstuffs and so forth, could be detected without any growth inhibition and microbial numbers could be measured accurately and quickly with Sample 1.

Based on the above results, it was found that the dried solid media of the conventional techniques required a long period of time for restoration and thus they were not suitable for quick and accurate measurement tests of microbial numbers.

In addition, when the test was repeated by changing the type of medium, the amount of medium poured into each dish, the amount of water (sterilized water) for restoration of dried solid medium and the restoration time of dried solid medium (within the range of 1 to 10 minutes), almost similar results were obtained.

TABLE 1

| Sample No. | Colony number of *Staphylococcus aureus* ATCC 6538P | Colony number of *Bacillus stearothermophilus* NIZO C953 |
|---|---|---|
| 1 | 102 | 98 |
| 2 | 35 | 38 |
| 3 | 40 | 53 |

Test Example 2

This test was performed in order to determine appropriate water content in solid medium by using results of microbial growth test as indexes.

(1) Preparation of Samples

Each of the following two kinds of samples was prepared in quintuplicate.

Sample 4: Solid medium prepared in the same manner as in Example 2 of the present invention except that solvent water was removed by drying so that the water content of the solid medium should become 90%

Sample 5: Solid medium prepared in the same manner as in Example 2 of the present invention except that solvent water was removed by drying so that the water content of the solid medium should become 80%

(2) Test Method

Microbial growth on each sample was examined in the same manner as the test method of Test Example 1 mentioned above except that only the *Staphylococcus aureus* ATCC 6538P mentioned above was used as a test strain.

Change of water content in the solid medium by drying was monitored in terms of weight loss caused by drying. That is, the weight loss by drying, i.e., so-called water loss (c), was obtained from weight of medium before drying (a) and weight of medium after drying (b) in accordance with the equation of a−b=c. Then, content of remaining water was obtained by subtracting the above water loss (c) from the weight of the total added solvent water. The water content after drying was obtained based on the definitions of the remaining water content and the aforementioned water content to monitor the change of water content of the solid medium by drying.

The solid medium composition of the mannitol sodium chloride agar medium is composed of 2.5 g of meat extract, 10 g of peptone, 75 g of sodium chloride, 10 g of mannitol, 0.025 g of Phenol Red, 15 g of agar and 1000 ml (prescribed amount of solvent water) of purified water.

(3) Test Results

The results of this test are as shown in Table 2. As clearly seen from the results shown in Table 2, when the water content of the solid medium was 80%, so-called less than 90%, growth of *Staphylococcus aureus* ATCC 6538P was almost completely inhibited, which made it impossible to count the microbial number, thus it was found that a water content of at least 90% was necessary to measure the numbers accurately.

In addition, when the test was repeated by changing the type of medium and the water content variously, almost similar results were obtained.

TABLE 2

| Sample No. | Colony number of *Staphylococcus aureus* ATCC 6538P |
|---|---|
| 4 | 97 |
| 5 | 0 |

Test Example 3

This test was performed by using the results of absorption rate test as indexes in order to determine an appropriate amount of solvent water to be removed (%) when an amount of solvent water described as a solid medium composition in literature and so forth was taken as 100%.

(1) Preparation of Samples

Each of the following four kinds of samples was prepared in quintuplicate.

Sample 6: Solid medium prepared in the same manner as in Example 1 of the present invention except that solvent water was not formulated in addition to the prescribed amount and removal of solvent water by drying was not performed Sample 7: Solid medium prepared in the same manner as in Example 1 of the present invention except that solvent water was additionally formulated by 2.5% of the prescribed amount and 2.5% of the total amount of solvent water was removed by drying.

Sample 8: Solid medium prepared in the same manner as in Example 1 of the present invention except that solvent water was additionally formulated by 5% of the prescribed amount and 5% of the total amount of solvent water was removed by drying.

Sample 9: Solid medium prepared in the same manner as in Example 1 of the present invention except that solvent water was additionally formulated by 40% of the prescribed amount and 30% of the total amount of solvent water was removed by drying.

(2) Test Method

The water absorption rate of each sample was determined by the following test method. The determination was performed at 25° C.

The total weight of sample plate (B) was measured, then 10 ml of ion exchanged water was added onto a plate medium (circular shape, outer diameter 9 cm. inner diameter: 8.6 cm (area: 58.1 cm$^2$), amount of medium: 15 g) to start water absorption; water not absorbed was discarded when 10 minutes passed; moisture on a dish wall was wiped off; and the total weight of the sample plate after water absorption (A) was measured. Then, the 10 minute-average water absorption rate was calculated in accordance with the following equation:

Water absorption rate (ml/minute)=$(A-B)/10$

Further, percentage of solvent water removed by drying (e) was obtained from the total amount of formulated solvent water (d) which was taken as 100%, and the water loss (c) monitored and calculated in the same manner as in Test Example 2 in accordance with the following equation:

$e(\%)=c/d\times 100$ (3) Test Results

The results of this test are as shown in Table 3. As clearly seen from the results shown in Table 3, when at least 5% of solvent water was removed by drying the medium, the water absorption rate became at least 0.05 ml/minute, and therefore it became possible to apply a large amount of a sample in a short period of time. Thus, it was found that it is necessary to remove at least 5% of solvent water for quick measurement tests of microbial numbers. Further, when at least 30% of solvent water was removed, the water absorption rate became at least 0.2 ml/minute, and therefore it became possible to apply a larger amount of the sample in a short period of time. Thus, it was found that it is preferable to remove at least 30% of solvent water for quick measurement tests of microbial numbers.

In addition, when the test was repeated by changing the type of medium variously, almost similar results were obtained.

TABLE 3

| Sample No. | 10 minute-average water absorption rate (ml/minute) |
| --- | --- |
| 6 | 0.02 |
| 7 | 0.04 |
| 8 | 0.06 |
| 9 | 0.2 |

INDUSTRIAL APPLICABILITY

The advantages of the present invention are as follows.
1) The medium of the present invention, which is prepared by the production method of the present invention, shows a superior water absorption rate, to enable application of a large amount of sample in a short period of time, and is suitable for quick measurement tests of microbial numbers.
2) Since the solid medium of the present invention, which is prepared by the production method of the present invention, enables application of a large amount of sample, it provides high accuracy for microbial detection and therefore it is suitable for accurate measurement tests of microbial numbers.
3) Since the solid medium of the present invention, which is prepared by the production method of the present invention, does not show growth inhibition due to drying, it is suitable for accurate measurement tests of microbial numbers.
4) A solid medium with a superior water absorption rate which enables application of a large amount of sample in a short period of time and suitable for quick and accurate measurement tests of microbial numbers can be prepared by the production method of the present invention.

What is claimed is:

1. A solid agar medium for microorganisms having a water content of at least 90%, and having a 10 minute-average water absorption rate of at least 0.05 ml/minute, which is obtainable by a method comprising the steps of:
    dissolving components of the solid medium other than solvent water into the solvent water,
    solidifying the obtained solution, and
    drying the solidified medium to remove water,
    wherein the 10-minute-average water absorption rate is calculated for an area of the medium which is about 58.1 cm$^2$ with a weight of about 15 gm, and wherein the amount of the solvent water is larger than a prescribed amount by an amount almost equal to the amount of the water to be removed.

2. The solid agar medium according to claim 1, wherein the amount of the removed water is at least 5% of the solvent water.

3. The solid agar medium according to claim 1, wherein the amount of the removed water to be removed is at least 30% of the solvent water.

4. A method for producing a solid agar medium for microorganisms which comprises the steps of:
    dissolving components of the solid agar medium into a solvent water,
    solidifying the obtained solution, and
    drying the solidified medium to remove water,
    wherein water is removed in such an amount that the solid medium after the removal of water should have a water content of at least 90%, and a 10 minute-average water absorption rate of at least 0.05 ml/minute calculated for an area of the medium which is about 58.1 cm$^2$ with a weight of about 15 gm, and wherein the amount of solvent water is larger than the prescribed amount by an amount almost equal to the amount of the removed water.

5. The method according to claim 4, wherein the amount of the removed water is at least 5% of the solvent water.

6. The method according to claim 4, wherein the amount of the removed water is at least 30% of the solvent water.

* * * * *